US006954513B2

(12) United States Patent
Horiuchi

(10) Patent No.: US 6,954,513 B2
(45) Date of Patent: Oct. 11, 2005

(54) X-RAY CT APPARATUS AND EXPOSURE DOSE CALCULATING METHOD

(75) Inventor: Tetsuya Horiuchi, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 99 days.

(21) Appl. No.: 10/738,754

(22) Filed: Dec. 17, 2003

(65) Prior Publication Data

US 2004/0131141 A1 Jul. 8, 2004

(30) Foreign Application Priority Data

Dec. 20, 2002 (JP) .................................... 2002-370591

(51) Int. Cl.⁷ ................................................ G21K 1/12
(52) U.S. Cl. ......................... 378/4; 378/98; 378/165
(58) Field of Search ............................. 378/4, 16, 18, 378/97, 98, 98.2, 108, 165, 207

(56) References Cited

U.S. PATENT DOCUMENTS 5,379,333 A 1/1995 Toth ........................... 378/16
6,141,398 A 10/2000 He et al. ....................... 378/4
6,141,402 A 10/2000 Toth ........................... 378/150
6,404,844 B1 6/2002 Horiuchi et al. ............... 378/8

FOREIGN PATENT DOCUMENTS

JP 2001-178713 7/2001

Primary Examiner—Edward J. Glick
Assistant Examiner—Courtney Thomas
(74) Attorney, Agent, or Firm—Carl B. Horton, Esq.; Armstrong Teasdale LLP

(57) ABSTRACT

For the purpose of displaying a more accurate exposure dose value without imposing additional work on an imaging operator, an exposure dose calculating method in an X-ray CT apparatus comprises the steps of: inputting the age and a region to be examined of a subject; calculating the head or chest diameter of the subject based on the age and region to be examined of the subject input at the inputting step, and on statistics on the head or chest circumference of a human body; calculating an exposure dose of a phantom having a diameter equivalent to the calculated diameter of the head or chest, based on prior information on an exposure dose to a phantom having a predetermined diameter when a predetermined X-ray dose is applied to the phantom; and displaying the exposure dose value.

9 Claims, 5 Drawing Sheets

FIG. 3

| Age | Statistical Data for Infant (Male) | | Statistical Data for Infant (Female) | |
|---|---|---|---|---|
| | Head | Circumference | Head | Circumference |
| 3 Months | . | . | . | . |
| 6 Months | 43.7 cm | . | . | . |
| 9 Months | . | . | . | . |
| 1 Year | . | . | . | . |
| . | . | . | . | . |
| . | . | . | . | . |
| . | . | . | . | . |

X-RAY CT APPARATUS AND EXPOSURE DOSE CALCULATING METHOD

CROSS REFERENCE TO RELATED APPLICATIONS

This application claims the benefit of Japanese Application No. 2002-370591 filed Dec. 20, 2002.

BACKGROUND OF THE INVENTION

The present invention relates to an X-ray CT (computerized tomography) apparatus for acquiring a tomographic image of a subject by X-ray irradiation.

An X-ray CT apparatus acquires (reconstructs) an image (X-ray tomographic image) of a cross-sectional plane (a plane at a slice position, i.e., slice plane) in an X-ray irradiated region in a subject (patient) by rotating an X-ray source for generating X-rays around the patient, detecting X-rays passing through the patient at different emission angles by an X-ray detector, and computer-processing the X-rays at an operation console.

When capturing the X-ray tomographic image of the patient using the X-ray CT apparatus, an exposure dose value (CTDI) that indicates the degree of exposure to the patient by the image capture is displayed on an operation console beforehand.

IEC and FDA recommend use of a value measured using a specified phantom as the exposure dose value displayed at that time. Specifically, when the head of the patient is imaged, there is employed a 16-cm acrylic phantom (see FIG. 5) provided with holes for inserting a measuring tool, one hole in the center and four near the outer periphery, and a value obtained by multiplying the dose (unit: [mGy]) measured with the measuring tool inserted into the holes by a prespecified weight is used as the displayed exposure dose. Similarly, when the body of the patient is imaged, a 32-cm acrylic phantom (not shown) is employed.

One technique for reducing the exposure dose to the subject to the minimum required amount is described in Patent Document 1.

Patent Document 1

Japanese Patent Application Laid Open No. 2001-178713.

The exposure dose value displayed when dividing only between the head and body and irrespective of the size of the patient body as in the conventional technique may, however, be different from the actual exposure dose value. Especially, when imaging the head or body of a pediatric patient that is smaller than the phantom for use in the measurement (for the head: 16 cm, and for the body: 32 cm), the exposure dose value displayed is susceptible to the risk of underestimation relative to the actual exposure dose value. Thus, it is desirable to display a measurement result from a phantom of a size that corresponds as close as possible to the outer periphery (head or chest circumference) of the X-ray irradiated region of the patient.

On the other hand, the work of measuring the outer periphery (head or chest circumference) of the imaged region for every patient before imaging, and inputting the result to the operation console puts an additional burden on the imaging operator (radiologist, physician, nurse or the like).

SUMMARY OF THE INVENTION

Therefore, an object of the present invention is to provide an X-ray CT apparatus that is capable of displaying a more accurate exposure dose value without imposing additional work to the imaging operator.

An X-ray CT apparatus in accordance with the present invention for solving the aforementioned problems comprises: a gantry comprising an X-ray source that generates a prespecified amount of X-rays and rotates around a subject and a detector for detecting X-rays passing through said subject at different emission angles, and an operation console for reconstructing an X-ray tomographic image of said subject based on data received from said gantry, said X-ray CT apparatus being characterized in comprising: input means for inputting information on said subject's age and information on an X-ray irradiated region in said subject; first storing means for storing statistics on the outer periphery lengths of regions in a human body binned with respect to information on age; second storing means for storing information on an exposure dose to a phantom having a predetermined diameter measured by irradiating said phantom with a predetermined X-ray dose in a predetermined time period; diameter calculating means for calculating a diameter of the X-ray irradiated region in said subject based on said information on the age of said subject and said information on the X-ray irradiated region in said subject input by said input means, and on said statistics on the outer periphery lengths stored in said first storing means; exposure dose calculating means for calculating an exposure dose to a phantom having a diameter equivalent to said calculated diameter of the X-ray irradiated region based on said information on the exposure dose stored in said second storing means; and display means for displaying said calculated exposure dose.

According to the present invention, a more accurate exposure dose value can be displayed without imposing additional work on the imaging operator.

Further objects and advantages of the present invention will be apparent from the following description of the preferred embodiments of the invention as illustrated in the accompanying drawings.

BRIEF DESCRIPTION OF THE DRAWINGS

FIG. 3 is a diagram showing the age—head circumference/chest circumference statistical data stored in the X-ray CT apparatus in accordance with the embodiment of the present invention.

DETAILED DESCRIPTION OF THE INVENTION

Several preferred embodiments of the present invention will now be described in detail with reference to the accompanying drawings. Similar reference symbols refer to identical or similar portions throughout the drawings.

<System Overall Configuration>

Figure 1:
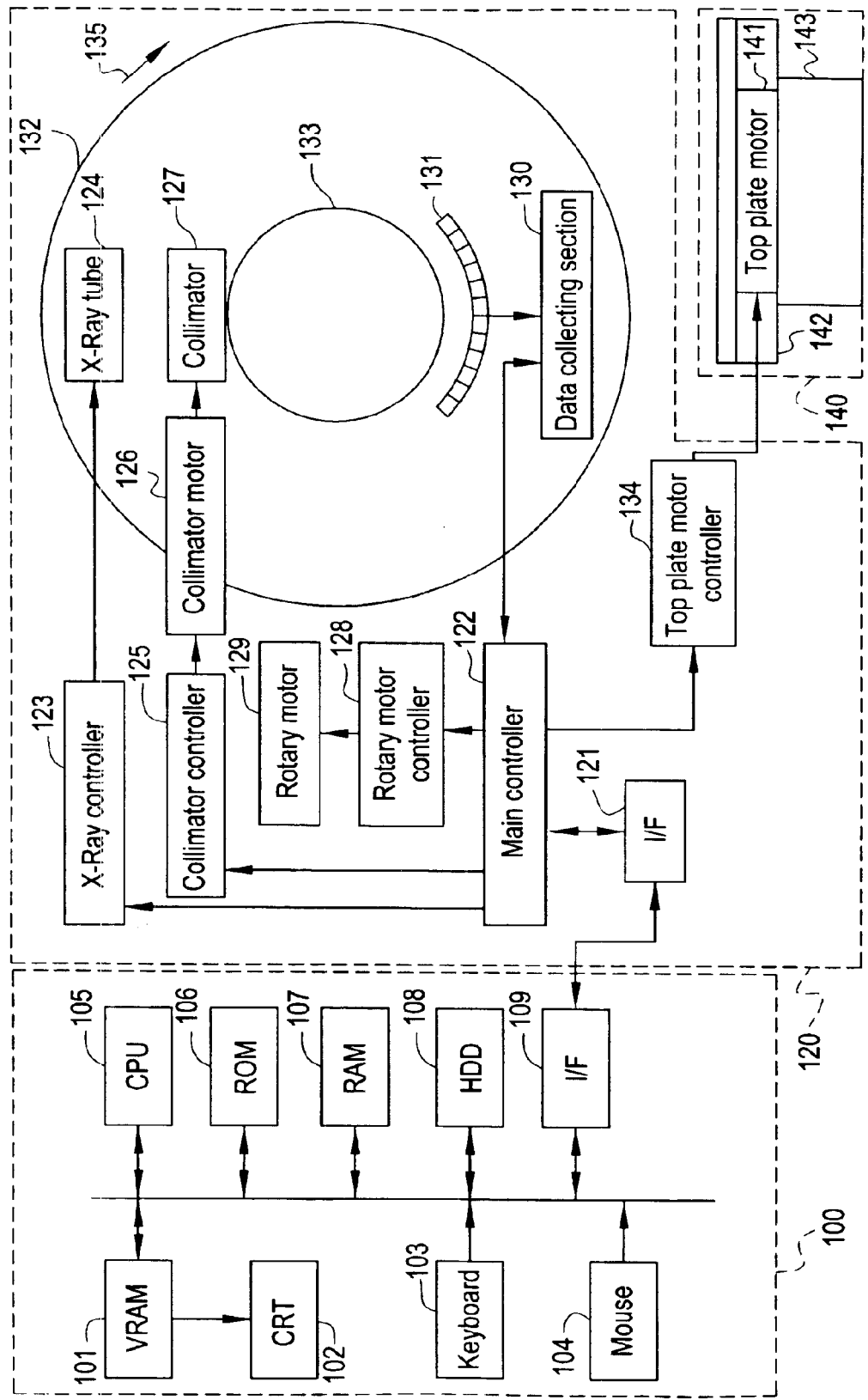
FIG. 1 is a diagram showing the configuration of an X-ray CT apparatus in accordance with one embodiment of the present invention.

FIG. 1 is a system configuration diagram of an X-ray CT apparatus in accordance with one embodiment of the present invention.

As shown in FIG. 1, the X-ray CT apparatus comprises a gantry 120 for irradiating a subject (patient) with X-rays and detecting X-rays passing through the borne subject, an operation console 100 for transmitting instruction signals to the gantry 120 to activate several kinds of settings, and reconstructing an X-ray tomographic image based on projection data output from the gantry 120 for display, and a carrier apparatus 140 for bearing thereon the subject and carrying the subject into the gantry.

The gantry designated by reference numeral 120 comprises a main controller 122 for conducting overall control along with the following components.

Reference numeral 121 designates an interface for communication with the operation console 100, reference numeral 132 designates a gantry rotating section provided therein with an X-ray tube 124 for generating X-rays (that is drive-controlled by an X-ray tube controller 123), a collimator 127 for defining the X-ray irradiation range, and a collimator motor 126 for adjusting the slit width of the collimator 127 to define the X-ray irradiation range and adjusting the position of the collimator 127 in the Z-axis direction (the direction perpendicular to the drawing plane i.e., the direction in which a top plate 142 described later is carried toward a cavity portion 133). Such driving by the collimator motor 126 is controlled by a collimator controller 125.

Moreover, the gantry rotating section designated by reference numeral 132 comprises an X-ray detecting section 131 for detecting X-rays passing through the subject, and a data collecting section 130 for collecting projection data acquired by the X-ray detecting section 131. The X-ray detecting section 131 comprises a plurality of detector rows arranged in the Z-axis direction, each row having a detector element group comprised of a plurality of detector elements (channels).

The X-ray tube 124 and collimator 127 and the X-ray detecting section 131 are opposingly disposed with respect to the cavity portion 133, and the gantry rotating section 132 is configured to rotate in a direction indicated by an arrow 135 while maintaining their mutual relationship. The rotation is conducted by a rotary motor 129 whose rotation speed is controlled by driving signals from the rotary motor controller 128 at a prespecified control cycle.

The carrier apparatus 140 has a top plate 142 on which the subject is directly rested and a table 143 for supporting the top plate 142. The top plate 142 is driven in the Z-axis direction by a top plate motor 141 (i.e., the direction of carrying the top plate=the Z-axis direction), and the drive of the top plate motor 141 at a carrying speed is controlled based on driving signals from a top plate motor controller 134 at a prespecified control cycle.

The main controller 122 analyzes several kinds of instruction signals received via the I/F 121, and based on the signals, outputs several kinds of control signals to the X-ray tube controller 123, collimator controller 125, rotary motor controller 128, top plate motor controller 134, and data collecting section 130. Moreover, the main controller 122 also executes processing for sending the projection data collected at the data collecting section 130 to the operation console 100 via the I/F 121.

The operation console 100 is what is generally called a workstation, and comprises a CPU 105 for conducting overall control for the entire apparatus, a ROM 106 storing a boot program, etc., a RAM 107 serving as a main storage device (memory), and the following components, as shown in FIG. 1.

HDD 108 is a hard disk device, and stores an OS and a diagnostic program for controlling the entire X-ray CT apparatus. The HDD 108 also stores a control program for causing the operation console 100 to execute the exposure dose calculating method in accordance with the present invention. The exposure dose calculating method in accordance with the present invention is achieved by the CPU 105 reading and executing the control program. At that time, a program code itself read from the HDD 108 implements the exposure dose calculating method, and the HDD 108 that stores the program code constitutes the present invention.

Returning to FIG. 1, a VRAM 101 is a memory for developing image data to be displayed (256×256 pixels), and the development of the image data, etc., on the VRAM 101 enables an X-ray tomographic image and a calculated exposure dose value (which will be described later) to be displayed on a CRT 102. Reference numerals 103 and 104 designate a keyboard and a mouse for several kinds of settings. Reference numeral 109 designates an interface for communication with the gantry 120.

<Flow of Exposure Dose Calculation Processing>

Figure 2:
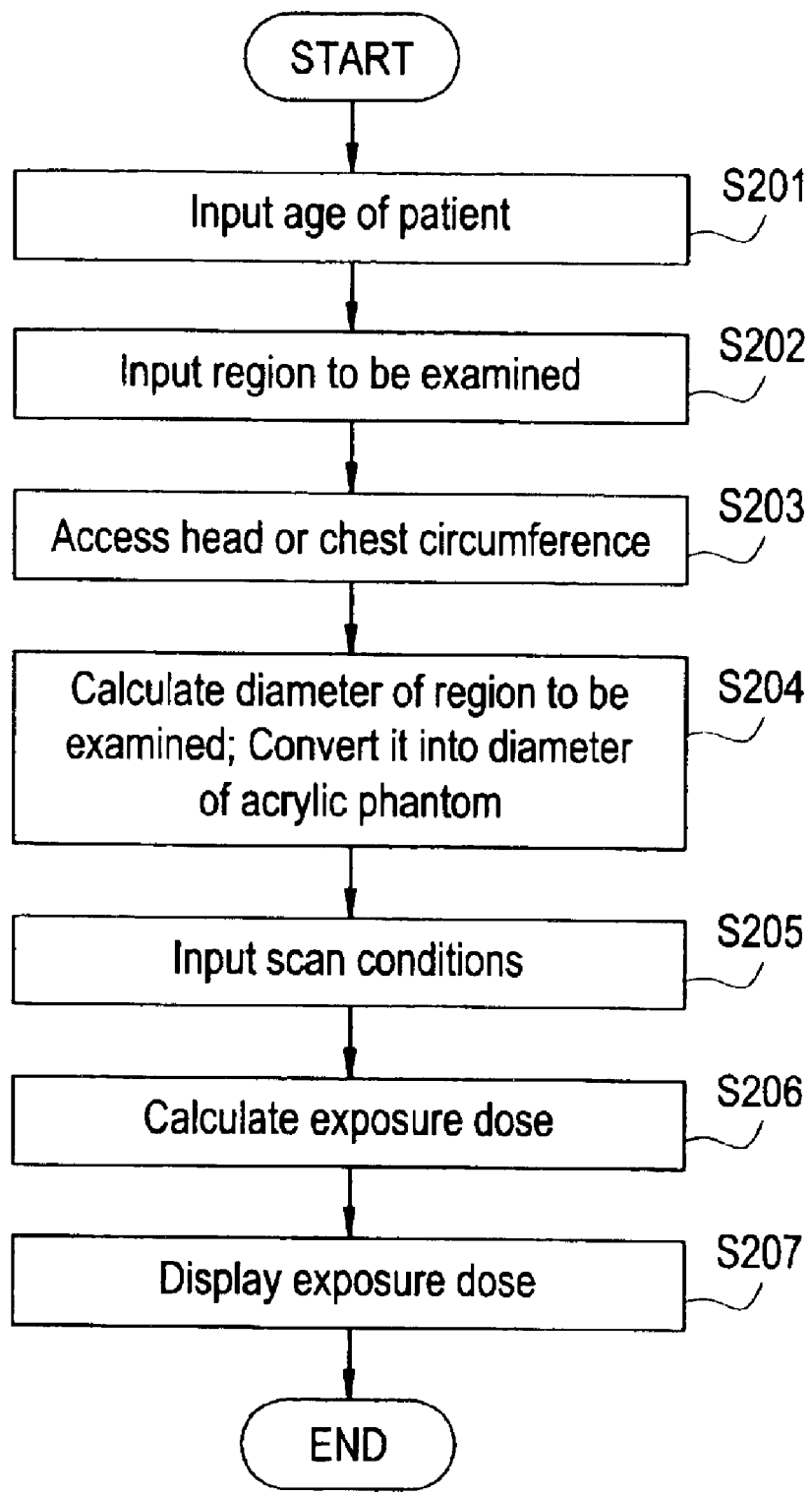
FIG. 2 is a flow chart showing processing for exposure dose value display in the X-ray CT apparatus in accordance with one embodiment of the present invention.

FIG. 2 is a flow chart showing exposure dose calculation processing in the X-ray CT apparatus in accordance with one embodiment of the present invention. The flow chart of FIG. 2 will be described hereinbelow with reference to FIGS. 3–5 as necessary.

At Steps S201 and S202, the age and a region to be examined (=X-ray irradiated region; particularly, the head or chest) of the patient are input using the keyboard 103 or mouse 104. It should be noted that the age and X-ray irradiated region of the patient are items that have been conventionally input when imaging the patient, and they are not newly required input items to implement the present invention (that is, the input operation does not impose additional work on the operator, and the work load does not change as compared with the conventional technique).

Based on the age and X-ray irradiated region of the patient input at Steps S201 and S202, a head or chest circumference corresponding to the size of the patient body is accessed (Step S203). The access to the head or chest circumference is conducted based on a table saved beforehand in the hard disk 108 in the operation console. FIG. 3 is an example of the table, and it allows derivation of a more realistic value by using, for example, statistical data of the age and the head and chest circumferences from a survey made by the Ministry of Health, Labour and Welfare. At Step S203, a head circumference is accessed if the X-ray irradiated region input at Step S202 is the head, and a chest circumference is accessed if the region is the chest.

Next, at Step S204, the diameter of an acrylic phantom is calculated based on the accessed head circumference (or chest circumference). Specifically, on the assumption that the head (or chest) is round, its diameter is calculated from the accessed head circumference (or chest circumference) (that is, the diameter is calculated by head circumference/π, or chest circumference/π).

If the tissue in the human body is assumed to be equivalent to water, then, by correcting the calculated diameter using a ratio between acrylic and water X-ray attenuations, an equivalent diameter of an acrylic phantom can be determined.

For example, the average head circumference of a six-month-old male infant is 43.7 cm according to FIG. 3. The diameter is about 13 cm assuming that the head is round as mentioned above. If the attenuation ratio between acrylic and water at a tube voltage of 120KV is about 0.9, an acrylic phantom diameter equivalent to the head of a six-month-old male infant is determined as about 12 cm.

At Step S205, several kinds of setting values in imaging the patient are read. Specifically, the setting values include a tube voltage, tube current, slice thickness, and gantry rotation speed.

Then, at Step S206, an exposure dose value is calculated. In calculating the exposure dose value, a graph representing a relationship between the acrylic phantom diameter and absorption dose as shown in FIG. 4 is referred to.

Figure 4:
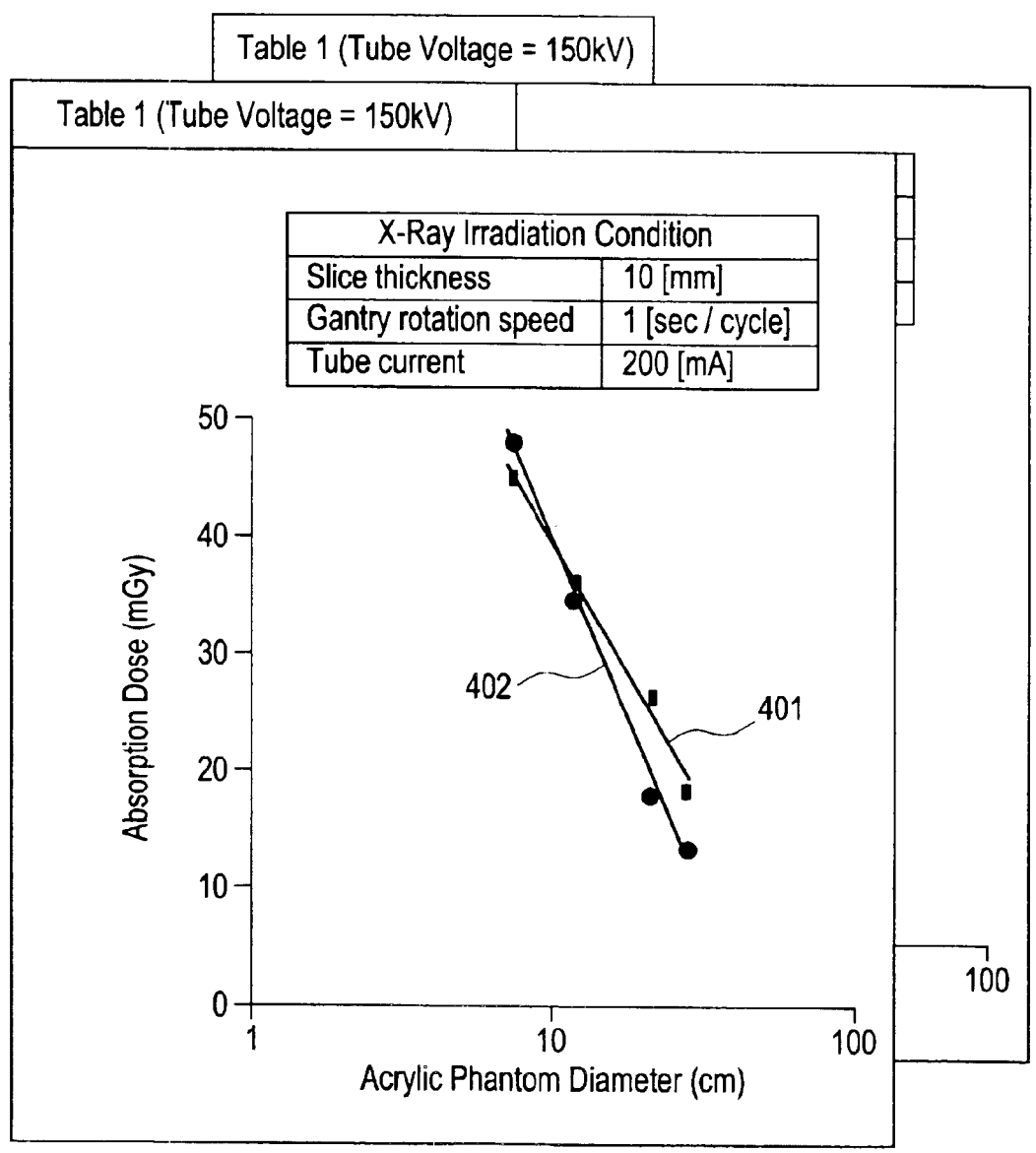
FIG. 4 is a diagram showing a relationship between an acrylic phantom diameter and an absorption dose.
Figure 5:
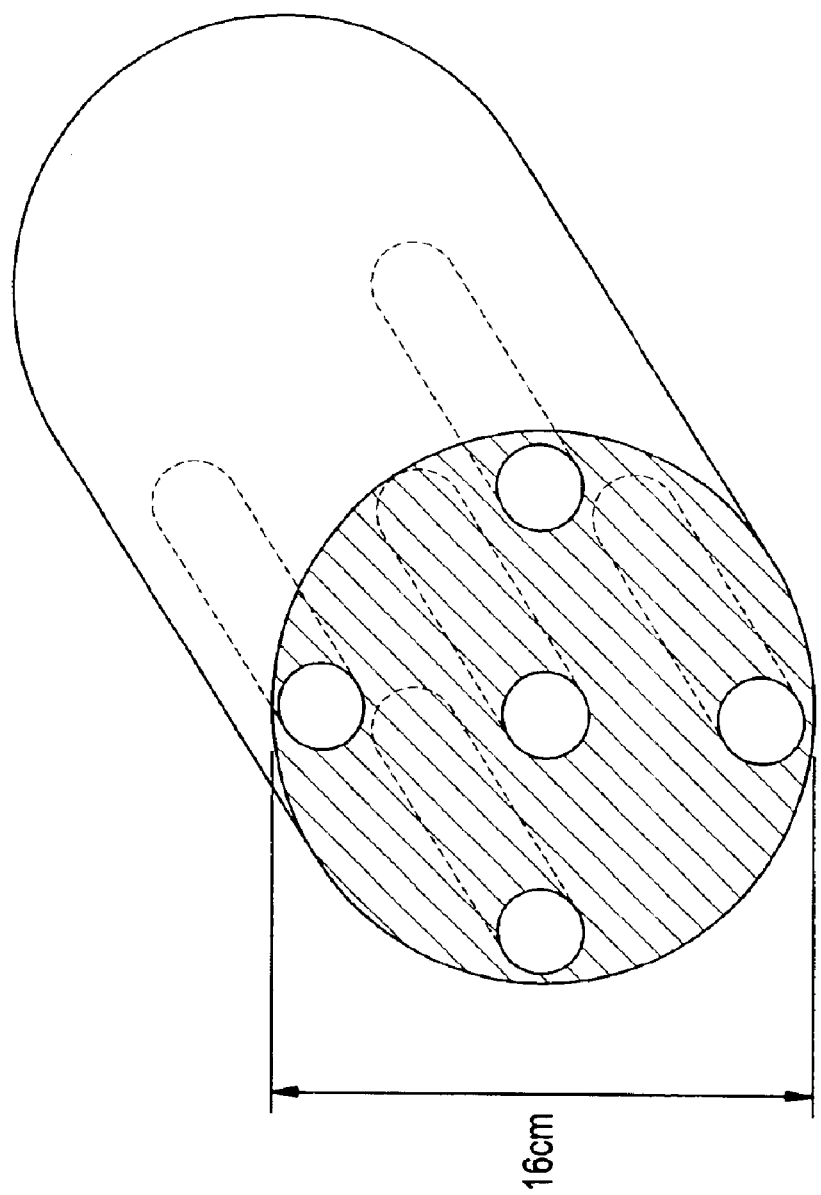
FIG. 5 is an exterior view of the acrylic phantom.

In FIG. 4, the horizontal axis represents the acrylic phantom diameter (cm), and the vertical axis represents the absorption dose (mGy) measured for each acrylic phantom diameter. Reference numeral 401 designates the absorption dose measured by a measurement tool inserted into a hole in the center of the acrylic phantom, and reference numeral 402 designates the absorption dose measured by the measurement tool inserted into a hole near the periphery of the acrylic phantom.

These values are measured beforehand for a plurality of tube voltages under a prespecified slice thickness, tube current and gantry rotation speed, are binned with respect to the tube voltages in the measurement process, and are stored along with the slice thickness, tube current and gantry rotation speed in the measurement process, as shown in FIG. 4.

A graph (one of those shown in FIG. 4) corresponding to the tube voltage read at Step S205 is referred to, and an absorption dose is calculated based on the acrylic phantom diameter calculated at Step S204. At that time, the tube current, slice thickness and gantry rotation speed read at Step S205 are used. That is, since the exposure dose value is proportional to the tube current, slice thickness and gantry rotation speed, a resultant exposure dose value is calculated from respective ratios of the tube current, slice thickness and gantry rotation speed read at Step S205 to a measurement condition (tube current, slice thickness, gantry rotation speed) in the referenced graph (FIG. 4).

The exposure dose value calculated at Step S206 is displayed on the operation console at Step S207. In the display, a value obtained by summing a weighted absorption dose 401 measured by the measurement tool inserted into the hole in the center of the acrylic phantom, and a weighted absorption dose 402 measured by the measurement tool inserted into the hole near the periphery of the acrylic phantom is displayed. In the present embodiment, the sum of the measured value in the center multiplied by 1/3 and the measured value in the peripheral portion multiplied by 2/3 is displayed as the exposure dose value.

As can be clearly seen from the preceding description, according to the present embodiment, by merely inputting the age and measured region of the patient as in the conventional technique, a more realistic exposure dose value than that in the conventional technique can be displayed.

Other Embodiments

Although an HDD is employed as a storage medium for supplying the program code in the aforementioned embodiment, the storage medium is not limited thereto but may be, for example, a floppy (registered trademark) disk, optical disk, magneto-optical disk, CD-ROM, CD-R, magnetic tape, non-volatile memory card, or ROM.

Moreover, it will be easily recognized that the present invention encompasses not only the case in which the function of the aforementioned embodiment is implemented by a computer reading and executing a program code but also the case in which the function of the aforementioned embodiment is implemented by an OS (operating system), for example, running on the computer, executing part or all of the actual processing based on instructions by the program code.

Furthermore, it will be easily recognized that the present invention encompasses the case in which the function of the aforementioned embodiment is implemented by writing the program code read out from a storage medium into a memory provided in a feature expansion board inserted into the computer or in a feature expansion unit connected to the computer, and then, executing part or all of actual processing based on instructions by the program code by a CPU provided in the extension board or unit.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray CT apparatus comprising:
   a gantry including an X-ray source that generates a prespecified amount of X-rays and rotates around a subject and a detector for detecting X-rays passing through said subject at different emission angles;
   an operation console for reconstructing an X-ray tomographic image of said subject based on data received from said gantry;
   an input device for inputting information on said subject's age and information on an X-ray irradiated region in said subject;
   a first storing device for storing statistics on the outer periphery lengths of regions in a human body binned with respect to information on age;
   a second storing device for storing information on an exposure dose to a phantom having a predetermined diameter measured by irradiating said phantom with a predetermined X-ray dose in a predetermined time period;
   a diameter calculating device for calculating a diameter of the X-ray irradiated region in said subject based on said information on the age of said subject and said information on the X-ray irradiated region in said subject input by said input device, and on said statistics on the outer periphery lengths stored in said first storing device;
   an exposure dose calculating device for calculating an exposure dose to a phantom having a diameter equivalent to said calculated diameter of the X-ray irradiated region based on said information on the exposure dose stored in said second storing device; and
   a display device for displaying said calculated exposure dose.

2. The X-ray CT apparatus of claim 1, wherein said second storing device stores said information on the exposure dose to said phantom for each tube voltage of the X-ray source in measuring said information.

3. The X-ray CT apparatus of claim 2, wherein said second storing device stores said information on the exposure dose to said phantom along with a tube current, slice thickness and gantry rotation speed of the X-ray source in measuring said information.

4. The X-ray CT apparatus of claim 3, wherein
   said apparatus further comprises setting device for setting a tube current, slice thickness and gantry rotation speed of the X-ray source in irradiating said subject with X-rays; and said exposure dose calculating device calculates said exposure dose based on respective ratios between the tube current, slice thickness and gantry rotation speed set by said setting device and the tube current, slice thickness and gantry rotation speed stored in said second storing device.

5. An exposure dose calculating method for an X-ray CT apparatus comprising a gantry including an X-ray source that generates a prespecified amount of X-rays and rotates around a subject and a detector for detecting X-rays passing through said subject at different emission angles, and an operation console for reconstructing an X-ray tomographic image of said subject based on data received from said gantry, comprising the steps of:

an inputting step for inputting information on said subject's age and information on an X-ray irradiated region in said subject;

a first storing step for storing statistics on the outer periphery lengths of regions in a human body binned with respect to information on age;

a second storing step for storing information on an exposure dose to a phantom having a predetermined diameter measured by irradiating said phantom with a predetermined X-ray dose in a predetermined time period;

a diameter calculating step for calculating a diameter of the X-ray irradiated region in said subject based on said information on the age of said subject and said information on the X-ray irradiated region in said subject input at said inputting step, and on said statistics on the outer periphery lengths stored at said first storing step;

an exposure dose calculating step for calculating an exposure dose to a phantom having a diameter equivalent to said calculated diameter of the X-ray irradiated region based on said information on the exposure dose stored at said second storing step; and a display step for displaying said calculated exposure dose.

6. The exposure dose calculating method of claim 5, wherein said second storing step stores said information on the exposure dose to said phantom for each tube voltage of the X-ray source in measuring said information.

7. The exposure dose calculating method of claim 6, wherein said second storing step stores said information on the exposure dose to said phantom along with a tube current, slice thickness and gantry rotation speed of the X-ray source in measuring said information.

8. The exposure dose calculating method of claim 7, wherein said method further comprises a setting step for setting a tube current, slice thickness and gantry rotation speed of the X-ray source in irradiating said subject with X-rays; and said exposure dose calculating step calculates said exposure dose based on respective ratios between the tube current, slice thickness and gantry rotation speed set at said setting step and the tube current, slice thickness and gantry rotation speed stored at said second storing step.

9. A control program embodied on a computer readable medium for calculating an exposure dose of a patient, said program configured to:

receive information on a subject's age and information on an X-ray irradiated region in the subject;

receive statistics on the outer periphery lengths of regions in a human body;

bin the information of the subject's age and the statistics on the outer periphery lengths in a common bin;

receive information on an exposure dose to a phantom having a predetermined diameter measured by irradiating the phantom with a predetermined X-ray dose in a predetermined time period;

calculate a diameter of the X-ray irradiated region in the subject based on the information on the age of the subject and the information on the X-ray irradiated region in the subject input, and on the statistics on the outer periphery lengths;

calculate an exposure dose for a phantom having a diameter equivalent to the calculated diameter of the X-ray irradiated region based on the information on the exposure dose; and display the calculated exposure dose.

* * * * *